(12) United States Patent
Caporaletti et al.

(10) Patent No.: US 6,686,027 B1
(45) Date of Patent: Feb. 3, 2004

(54) SECURITY SUBSTRATE FOR DOCUMENTS OF VALUE

(75) Inventors: Omar Caporaletti, Mississauga (CA); John Nicholas Disano, Ottawa (CA); Jack Scott, Oakville (CA)

(73) Assignee: Agra Vadeko Inc., Oakville (CA)

( * ) Notice: Subject to any disclaimer, the term of this patent is extended or adjusted under 35 U.S.C. 154(b) by 0 days.

(21) Appl. No.: 09/669,425

(22) Filed: Sep. 25, 2000

(51) Int. Cl.[7] .................. B32B 23/02; B32B 27/08; B32B 11/06; B32B 15/04; B41M 3/12
(52) U.S. Cl. ............. 428/195; 428/515; 428/491; 428/457; 427/146; 283/91; 283/72; 283/83
(58) Field of Search .................. 428/195, 515, 428/491, 457; 427/146; 283/91, 72, 83

(56) References Cited

U.S. PATENT DOCUMENTS

| | | | |
|---|---|---|---|
| 3,858,977 A | 1/1975 | Baird et al. .................. 356/71 |
| 4,749,591 A | 6/1988 | Ronchi ......................... 427/79 |
| 4,952,420 A | 8/1990 | Walters ........................ 427/97 |
| 4,962,725 A | 10/1990 | Heinz et al. ................ 118/718 |
| 5,223,038 A | 6/1993 | Kleyer ......................... 118/718 |
| 5,350,598 A | 9/1994 | Kleyer ...................... 427/255.5 |
| 5,425,996 A | * 6/1995 | Wilkie et al. ................ 428/457 |
| 5,492,370 A | * 2/1996 | Chatwin et al. ............. 283/110 |
| 5,935,696 A | 8/1999 | Benoit et al. ................ 428/219 |
| 6,294,267 B1 | * 9/2001 | Benoit ........................ 428/515 |
| 6,318,758 B1 | * 11/2001 | Stenzel et al. ................ 283/91 |

* cited by examiner

*Primary Examiner*—Cynthia H. Kelly
*Assistant Examiner*—J. Ferguson
(74) *Attorney, Agent, or Firm*—Baker & Daniels

(57) ABSTRACT

A security substrate for a document of value comprises a laminate including a generally transparent core layer and generally transparent outer layers on opposite sides of the core layer. At least one interference filter is embedded within the laminate. The interference filter includes a highly reflective opaque layer on a surface of the core layer and an optically variable thin film multilayer overlying at least a portion of the opaque layer. The interference filter is covered by one of the outer layers.

26 Claims, 2 Drawing Sheets

SECURITY SUBSTRATE FOR DOCUMENTS OF VALUE

FIELD OF THE INVENTION

The present invention relates to document security and in particular to a security substrate for documents of value such as for example, banknotes, credit cards, identification cards and the like.

BACKGROUND OF THE INVENTION

Documents of value such as identification cards, credit cards, banknotes, etc. are in many cases formed of polymer-based laminates. For example, U.S. Pat. No. 5,935,696 to Benoit et al. discloses a laminated multilayer film substrate having high-density polyethylene layers on each side of an oriented polypropylene layer. The multilayer film substrate exhibits good embossability, dead-fold characteristics and other properties making it suitable for the production of banknotes and other security documents.

Marking documents of value is common practice to deter forgery and allow counterfeit cards and banknotes to be readily detected. For example, U.S. Pat. No. 3,858,977 to Baird et al. discloses an optical interference filter having an optical interference layer with a known characteristic of spectral reflectance and a different known characteristic of spectral transmittance, both of which vary with the angle of incident light on the interference filter. The interference filter is disposed on the banknote substrate over a coloured portion thereof designed to absorb some of the light transmitted by the interference filter so that the interference filer exhibits a colour change with a change in the angle of incident light.

In order to inhibit forgery and counterfeiting, it is desired that security features used to mark documents of value be difficult to copy and highly secured against alteration. Accordingly, improved substrates for documents of value are desired.

It is therefore an object of the present invention to provide a novel security substrate for a document of value and method of forming the same.

SUMMARY OF THE INVENTION

According to one aspect of the present invention there is provided a security substrate for a document of value comprising:

a laminate including a generally transparent core layer and a generally transparent outer layer on at least one side of said core layer; and at least one interference filter embedded within said laminate, said interference layer including a highly reflective opaque layer on a surface of said core layer and an optically variable thin film multilayer overlying at least a portion of said opaque layer, said interference filter being covered by said outer layer.

In a preferred embodiment, the opaque metal layer is patterned on the core layer at spaced locations. The opaque metal layer can be patterned to form continuous stripes or discrete elements that may or may not be intricately patterned.

Preferably, the optically variable thin film multilayer includes one or more dielectric film layers of low refractive index and a semi-transparent, medium reflective layer.

Preferably, generally transparent outer layers are provided on opposite sides of the core layer. Opacifying coatings can be applied to the outer layers and have windows formed therein that are in registration with the interference filter.

According to another aspect of the present invention there is provided a security substrate for a document of value comprising:

a laminate including a generally transparent balanced biaxially oriented core layer, said core layer being oriented in at least a first direction at an orientation ratio of at least 4:1 and oriented in a second direction substantially normal to the first direction at an orientation ratio of at least 6:1; generally transparent imbalanced biaxially oriented outer layers on opposite sides of said core layer, said outer layers being oriented in at least a first direction to a degree which is at least three times less than the degree of orientation present in a second direction substantially normal to the first direction; and a laminating adhesive resin disposed between the outer layers and the core layer to secure the outer layers to the core layer so that the first directions of orientation of the outer layers are substantially aligned;

at least one optically variable device embedded within the laminate, the at least one optically variable device including a highly reflective opaque layer on a surface of said core layer and an optically variable thin film multilayer overlying at least a portion of the opaque layer, said at least one optically variable device being covered by one of said outer layers; and opacifying coatings on said outer layers, at least one window being formed in at least one of said opacifying coatings that is in registration with said at least one optically variable device.

According to another aspect of the present invention there is provided a method of forming a security substrate for a document of value comprising the steps of:

depositing a highly reflective opaque layer on a surface of a generally transparent core layer;

depositing an optically variable thin film multilayer on said core layer to overlie at least a portion of said opaque layer; and overlying at least one side of said core layer with a generally transparent outer layer to cover said opaque layer and optically variable thin film multilayer thereby to embed an optically variable device within said security substrate The present invention provides advantages in that the optically variable interference filter is embedded in the security substrate protecting it from mechanical and chemical attack as well as wear and tear. As a result, the security substrate exhibits high longevity and is highly secured against alternation. Also, since the optically variable interference filter exhibits a sharp color shifting characteristic with changes in the angle of view, the security substrate is virtually impossible to counterfeit using digital methods, laser scanning or photocopying. Furthermore, the security substrate exhibits high tensile strength in the oriented and unoriented directions, good folding and crumple resistance.

BRIEF DESCRIPTION OF THE DRAWINGS

Embodiments of the present invention will now be described more fully with reference to the accompanying drawings in which.

DETAILED DESCRIPTION OF THE PREFERRED EMBODIMENTS

Figure 1:
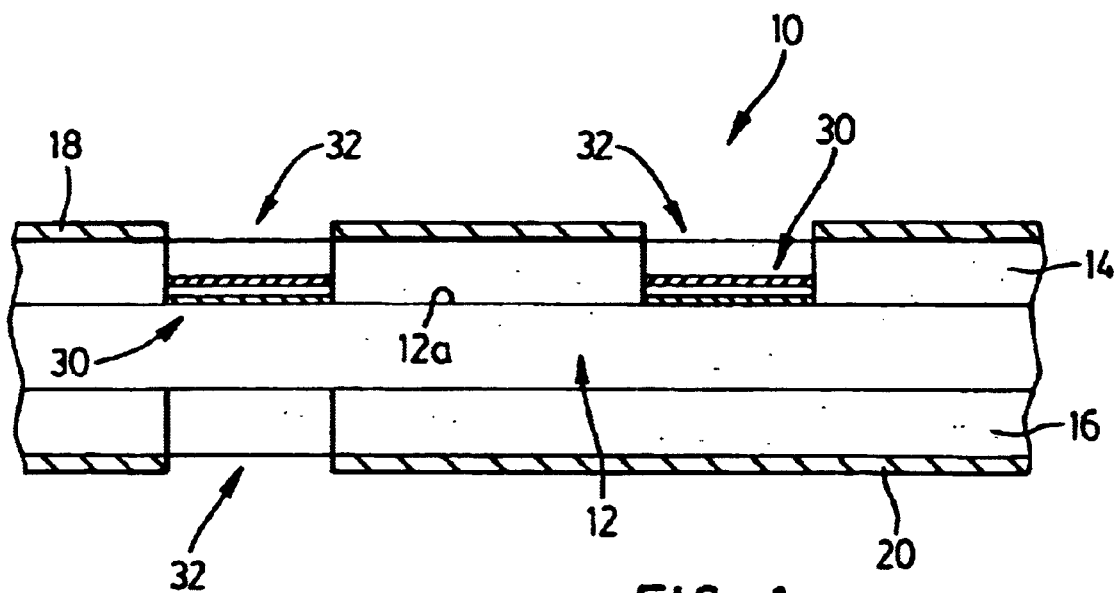
FIG. 1 is a cross-sectional view of a security substrate in accordance with the present invention.

Turning now to FIG. 1, a security substrate in accordance with the present invention is shown and is generally indicated to by reference numeral 10. As can be seen, security substrate 10 includes a generally transparent central core layer 12 formed of oriented polypropylene (OPP) disposed between generally transparent, high-density polyethylene (HDPE) layers 14 and 16. The HDPE layers 14 and 16 are secured to the OPP core layer 12 by laminating adhesive resin. Opacifying coatings 18 and 20 designed to accept printed indicia cover the HDPE layers 14 and 16. Optically variable devices in the form of interference filters 30 are embedded within the security substrate 10. The interference filters 30 in this example are disposed on one surface 12a of the OPP core layer 12 and are covered by the HDPE layer 14. It will however be appreciated that the interference filters may be disposed on either or both sides of the OPP core layer 12. Windows 32 are formed in the opacifying coatings 18 and 20 at locations corresponding to the positions of (i.e. in registration with) the interference filters 30. Depending on the desired effect, the windows can be formed in one or both opacifying coatings 18 and 20.

In the present embodiment, the OPP and HDPE layers 12, 14 and 16 respectively form a multilayer substrate similar to that disclosed in U.S. Pat. No. 5,935,696 to Benoit et al, the contents of which are incorporated herein by reference. Thus, the HDPE layers 14 and 16 are imbalanced biaxially and are oriented in a first direction to a degree that is at least three times less than the degree of orientation in a second direction normal to the first direction. The OPP core layer 12 is balanced biaxially and is oriented in a first direction at an orientation ratio of at least 4:1 and oriented in at least a second direction normal to the first direction at an orientation ratio of at least 6:1. The HDPE layers 14 and 16 are arranged such that their orientations in the first directions are aligned.

In the present embodiment, the interference filters 30 include highly reflective opaque metal stripes 50 formed of aluminum that are disposed on the surface 12a of OPP core layer 12 (see FIG. 2) and optically variable thin film multilayers 52 disposed on the opaque metal stripes 50. The opaque metal stripes 50 preferably have a reflectance greater than 90% at a 500 nm wavelength and an optical density in the range from about 2.0 and 3.0.

The opaque metal stripes 50 are patterned on the surface 12a of the OPP core layer 12. A number of techniques can be used to pattern the opaque metal stripes 50 on the OPP core layer 12. For example, the opaque metal stripes 50 may be patterned on the OPP core layer 12 using an oil patterning process such as those described in U.S. Pat. No. 4,749,591 to Ronchi; U.S. Pat. No. 4,952,420 to Walters; U.S. Pat. No. 4,962,725 to Heinz et al.; U.S. Pat. No. 5,223,038 to Kleyer; and U.S. Pat. No. 5,350,598 to Kleyer. During this process a layer of suitable oil is deposited on the OPP core layer 12 prior to vacuum evaporization of the opaque metal stripes on the OPP core layer. The oil is applied to the OPP core layer 12 in a vacuum in the evaporization system to create areas where the opaque metal will not nucleate. In this manner, an etchless patterning method for the opaque metal is achieved.

Alternatively, the opaque metal stripes 50 may be evaporated as thin films onto the surface 12a of the OPP core layer 12 through a physical mask as is well known.

The opaque metal stripes may also be patterned on the surface 12a of the OPP core layer 12 through demetallization using one of two techniques. In one technique, an alkaline etchant solution is printed directly onto the opaque metal in selected areas. The residue is then washed away leaving the patterned metal, which is then evaporated onto the OPP core layer 12. In another technique, the opaque metal is evaporated onto the OPP core layer 12. A mask in the shape of the desired pattern is then placed over the opaque metal and an alkaline etchant solution is printed directly onto the exposed opaque metal. The residue is then washed away and the mask is removed leaving the patterned opaque metal. Using either of these demetallization techniques allows intricate opaque metal patterns to be placed on the OPP core layer 12 with features less than 100 microns in size.

The opaque metal stripes 50 may also be printed on the surface 12a of the OPP core layer 12 using metallic high reflectance inks.

Figure 3:
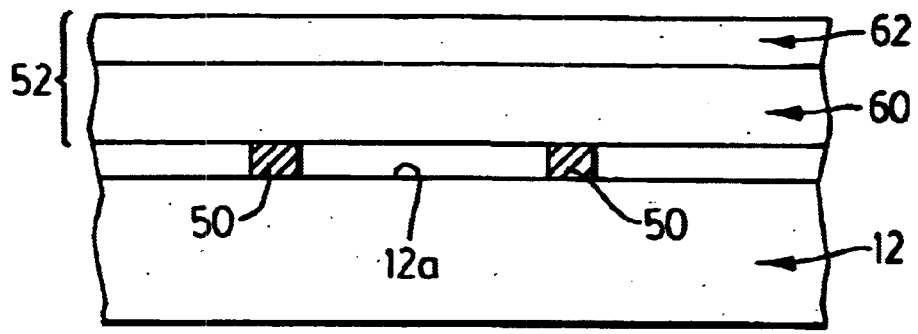
FIG. 3 is a cross-sectional view of the core layer of FIG. 2 coated with an optically variable thin film multilayer.

Each optically variable thin film multilayer 52 includes one or more layers of a low refractive index dielectric film identified collectively by reference numeral 60 such as for example, $SiO_2$, $MgF_2$, $Al_2O_3$ etc. or acrylate-based organic compounds, together with a semi-transparent, medium reflective metal layer such as aluminum or alloy such as Inconel (Ni/Cr/Fe alloy) 62 (see FIG. 3). The layers 60 of dielectric film are evaporated, sputtered or deposited by chemical vapour deposition (CVD) on the OPP core layer 12 over portions of the opaque metal stripes 50. If an Inconel layer is used, the thickness of the layer is preferably about 10 nm. If $SiO_2$ dielectric films are used, the thickness of the films is preferably in the range of about 170 nm to 480 nm. If $Al_2O_3$ dielectric films are used, the thickness of the films is preferably in the range of from about 200 nm to 470 nm. At locations where the optically variable thin film multilayers 52 cover the opaque metal stripes 50, interference filters 30 are formed that exhibit sharp color shifting characteristics with change in the angle of view.

The interference filters 30 have well defined characteristics of spectral reflectance and transmittance, both of which vary with the angle of incident of light. As a result, the interference filters 30 provide a sharp color shift that changes with the angle of view. The spectral characteristics are of course dependent on the optical constants, refractive indices, absorption coefficients and thicknesses of the security substrate layers. Depending on whether the interference filters 30 are exposed by a window 32 in one opacifying coating 18 or 20 or windows 32 in both opacifying coatings 18 and 20, different optical effects are achieved. If windows 32 are provided in both opacifying coatings 18 and 20, an observer sees an optically variable effect through the window 32 in opacifying coating 18 and a reflective metallic image through the window 32 in opacifying coating 20 that is in registration with the optically variable effect. If a window 32 is only provided in the opacifying coating 18, only the optically variable effect is visible. If a window 32 is only provided in the opacifying coating 20, only the reflective metallic image is visible.

Figure 2:
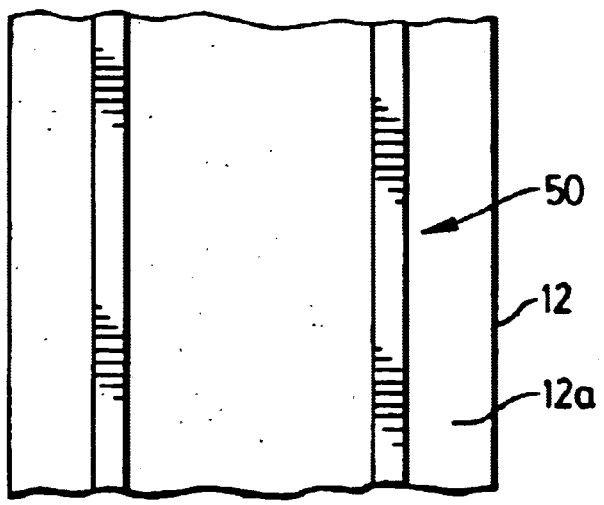
FIG. 2 is a top plan view of a core layer having highly reflective opaque metal stripes thereon forming part of the security substrate of FIG. 1.
Figure 4:
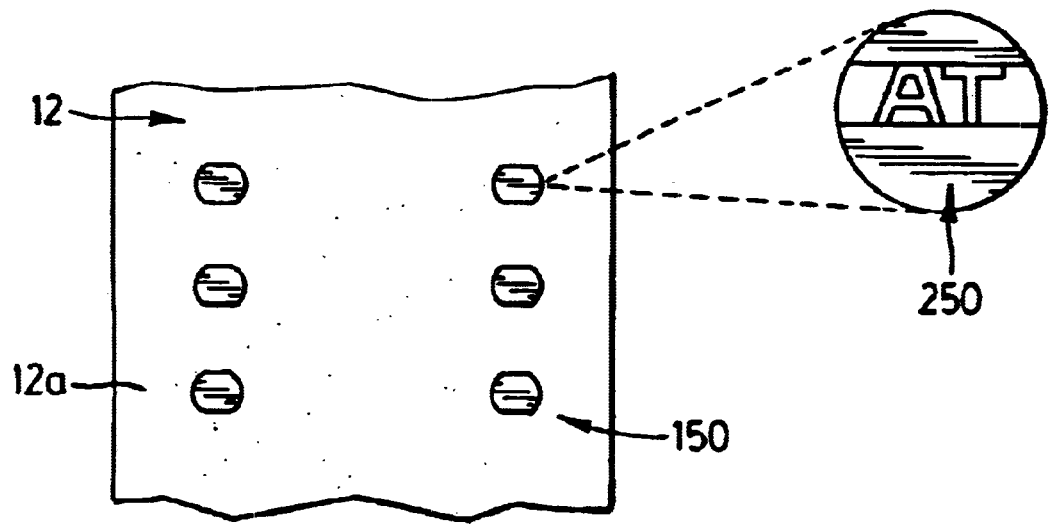
FIG. 4 is a top plan view of another embodiment of the core layer having discrete highly reflective opaque metal elements thereon.

The opaque metal disposed on the OPP core layer 12 need not take the form of stripes 50 as shown in FIG. 2. For example, as shown in FIG. 4, the opaque metal can be deposited on the surface 12a of OPP core layer 12 at discrete locations as discrete elements 150 or in intricate patterns 250.

Although the security substrate 10 is described as including an OPP core layer 12, other biaxially oriented polymers of comparable tensile strength such as linear low-density polyethylene (LLDPE), nylons or polyesters may be used. In cases where high evaporation temperatures are used, PET is preferred.

Also, although preferred embodiments of the present invention have been described, those of skill in the art will appreciate that variations and/or modifications may be made without departing from the spirit and scope thereof as defined by the appended claims.

What is claimed is:

1. A security substrate for a document of value comprising:
    a laminate having a generally transparent core layer and a generally transparent outer layer on at least one side of said core layer; and
    at least one interference filter embedded within said laminate between said core layer and said outer layer, said interference filter having a highly reflective opaque layer on a surface of said core layer and an optically variable thin film multilayer overlying at least a portion of said opaque layer.

2. A security substrate as defined in claim 1 wherein said opaque layer is patterned on said core layer.

3. A security substrate as defined in claim 2 wherein said opaque layer is patterned on said core layer at spaced locations.

4. A security substrate as defined in claim 3 wherein said opaque layer is patterned to form continuous stripes on said core layer.

5. A security substrate as defined in claim 3 wherein said opaque layer is patterned to form discrete elements on said core layer.

6. A security substrate as defined in claim 5 wherein said discrete elements are individually patterned.

7. A security substrate as defined in claim 3 wherein said opaque layer is formed of aluminum having a reflectance greater than 90% and an optical density in the range of from about 2.0 to 3.0.

8. A security substrate as defined in claim 2 wherein said optically variable thin film multilayer includes one or more dielectric film layers of low refractive index and a semi-transparent, medium reflective layer overlying said one or more dielectric film layers.

9. A security substrate as defined in claim 8 wherein said one or more dielectric film layers is selected from the group consisting of $SiO_2$, $MgF_2$, $Al_2O_3$, and acrylate based organic compounds and wherein said medium reflective layer is selected from the group consisting of semi-transparent metals and semi-transparent alloys.

10. A security substrate as defined in claim 9 wherein said semi-transparent metals include aluminum and wherein said semi-transparent alloys include Ni/Cr/Fe.

11. A security substrate as defined in claim 1 wherein said laminate includes generally transparent outer layers on opposite sides of said core layer and wherein said security substrate further includes opacifying coatings on said outer layers, at least one window being formed in one of said opacifying coatings that is in at a location corresponding to said at least one interference filter.

12. A security substrate as defined in claim 11 wherein windows are formed in both opacifying coatings that are at locations corresponding to said at least one interference filter.

13. A security substrate as defined in claim 2 wherein said core layer is formed of oriented polypropylene and wherein said outer layer is formed of high-density polyethylene.

14. A security substrate as defined in claim 11 in the form of a banknote.

15. A security substrate for a document of value comprising:
    a laminate having a generally transparent balanced biaxially oriented core layer, said core layer being oriented in at least a first direction at an orientation ratio of at least 4:1 and oriented in a second direction substantially normal to the first direction at an orientation ratio of at least 6:1; generally transparent imbalanced biaxially oriented outer layers on opposite sides of said core layer, said outer layers being oriented in at least a first direction to a degree which is at least three times less than the degree of orientation present in a second direction substantially normal to the first direction; and a laminating adhesive resin securing the outer layers to the core layer so that the first directions of orientation of the outer layers are substantially aligned;
    at least one optically variable device embedded within the laminate between said core layer and one of said cover layers, the at least one optically variable device having a highly reflective opaque layer on a surface of said core layer and an optically variable thin film multilayer overlying at least a portion of the opaque layer; and
    opacifying coatings on said outer layers, at least one window being formed in at least one of said opacifying coatings that is at a location corresponding to said at least one optically variable device.

16. A security substrate as defined in claim 15 in the form of a banknote.

17. A security substrate as defined in claim 16 wherein said opaque layer is patterned on said core layer.

18. A security substrate as defined in claim 17 wherein said opaque layer is formed of aluminum having a reflectance greater than 90% and an optical density in the range of from about 2.0 to 3.0.

19. A security substrate as defined in claim 18 wherein said optically variable thin film multilayer includes one or more dielectric film layers of low refractive index and a semi-transparent, medium reflective layer overlying said one or more dielectric film layers.

20. A security substrate as defined in claim 18 wherein said one or more dielectric film layers is selected from the group consisting of $SiO_2$, $MgF_2$, $Al_2O_3$, and acrylate based organic compounds and wherein said medium reflective layer is selected from the group consisting of semi-transparent metals and semi-transparent alloys.

21. A security substrate as defined in claim 20 wherein said semi-transparent metals include aluminum and wherein said semi-transparent alloys include Ni/Cr/Fe.

22. A security substrate as defined in claim 1 wherein said opaque layer is formed of metallic high reflectance ink.

23. A security substrate as defined in claim 16 wherein said opaque layer is formed of metallic high reflectance ink.

24. A security substrate as defined in claim 16 wherein windows are formed in both of said opacifying coatings at locations corresponding to said at least one optically variable devices.

25. A security substrate as defined in claim 16 including a plurality of optically variable devices embedded within said laminate between said core layer and an outer layer at discrete locations, a window being formed in said opacifying coatings for each of said optically variable devices.

26. A security substrate as defined in claim 25 wherein windows are formed in both of said opacifying coatings for at least one of said optically variable devices.

* * * * *